United States Patent [19]

Matsuo

[11] Patent Number: 4,682,586
[45] Date of Patent: Jul. 28, 1987

[54] AUTOMATIC EXPOSURE CONTROL DEVICE FOR ENDOSCOPE

[75] Inventor: Kazumasa Matsuo, Tokyo, Japan

[73] Assignee: Olympus Optical Co., Ltd., Tokyo, Japan

[21] Appl. No.: 657,476

[22] Filed: Oct. 4, 1984

Related U.S. Application Data

[63] Continuation of Ser. No. 54,881, Jul. 5, 1979.

[51] Int. Cl.$^4$ ............................................. A61B 1/06
[52] U.S. Cl. .......................................... 128/6; 354/62
[58] Field of Search ........................................ 128/4–8; 354/42, 46, 49, 50, 51, 59, 62, 286

[56] References Cited

U.S. PATENT DOCUMENTS

| | | | |
|---|---|---|---|
| 2,280,561 | 4/1942 | Wappler | 128/4 |
| 3,486,434 | 12/1969 | Suzuki et al. | 354/46 |
| 3,678,823 | 7/1972 | Sato | 354/49 |
| 3,713,369 | 1/1973 | Fuji | 354/59 |
| 3,782,261 | 1/1974 | Araki | 354/286 |
| 4,153,356 | 5/1979 | Hama | 128/8 |

FOREIGN PATENT DOCUMENTS

2139711  5/1972  Fed. Rep. of Germany ........ 354/49

*Primary Examiner*—Edward M. Coven
*Assistant Examiner*—Max F. Hindenburg

[57] ABSTRACT

An endoscope-use camera attached to the eyepiece section of an endoscope has conventionally been provided with an automatic exposure control device including a light sensing element and capable of automatically determining an exposure value in accordance with a quantity of light received. Disclosed herein is an automatic exposure control device which further comprises a control member disposed at the eyepiece section of an endoscope and having a shape depending on the thickness of an image transmitting optical system, and a device for determining in cooperation with the control member the correction value for an exposure value in accordance with the thickness of the image guide when the endoscope is attached to the camera.

2 Claims, 13 Drawing Figures

AUTOMATIC EXPOSURE CONTROL DEVICE FOR ENDOSCOPE

This application is a continuation, of application Ser. No. 054, 881, filed July 5, 1979.

BACKGROUND OF THE INVENTION

This invention relates to an automatic exposure control device for endoscope of a mean photometry type.

An endoscope is generally used for observations inside living body cavities or precision machines. The endoscope is composed of an objective section, an eyepiece section, and a coupling section for optically connecting these two sections. A light source for forming a subject image by means of an objective of the objective section may be disposed externally and coupled to the objective section by means of a light guide formed of glass fiber, or disposed directly inside the objective section. The subject image provided by the objective is transmitted to an eyepiece through an image transmitting optical system, and observed. In photographing the subject image, a camera has usually been attached to the eyepiece section for the convenience of observation. When using an expensive fiber scope in photographing, the eyepiece section is provided with a light sensing element for each unit of endoscope, and a signal is sent to the light source unit in accordance with a quantity of light passed through the eyepiece section, and the light supply to the light source unit is controlled automatically when a proper exposure value is reached. When using a low-priced rigid endoscope, on the other hand, the light sensing element is not provided for each unit of endoscope, and the exposure control is conducted manually by experience. Thereupon, the endoscope is subject to different thicknesses of the image transmitting optical system and different magnifications of the eyepiece depending on a applications. That is, the size of the subject image on a film surface is generally smaller than that of the film surface due to the effect of brightness, varying with the type of endoscope. As a result, in a photometer circuit of a mean photometry type, the photometric quantity (detected by the light sensing element) varies with the size of the subject image even though the same illuminance is obtained for the unit area on the film surface. If the subject image appears only on part of the film surface, for example, the quantity of light sensed will be levelled to provide a photometric quantity level lower than the actual level of illumination.

Namely, the use of a narrow endoscope (where the subject image on the film is small) causes overexposure. Accordingly, when using endoscopes of different thicknesses in combination with a photographing/light source unit capable of automatic exposure control (in accordance with the quantity of light sensed), the exposure control circuit must be supplied with correction information in accordance with the thickness of the endoscope (size of subject image). However, there are so many types of endoscopes that it is quite troublesome and mistakable for a user to switch the automatic exposure control circuit of the camera selectively in accordance with the thickness of the endoscope every time he uses the device. Moreover, the manual switching of the automatic exposure control circuit by the user may halve the advantages of automatic exposure.

SUMMARY OF THE INVENTION

The object of this invention is to provide an automatic exposure control device for an endoscope attached to an eyepiece section of the endoscope and capable of photographing a subject image obtained by means of an objective and transmitted to an eyepiece through an image transmitting optical system with an optimum exposure value automatically provided in accordance with the brightness of the subject image.

The above object may be attained by an automatic exposure control device for an endoscope light source unit which comprises a means located at an eyepiece section of an endoscope and holding information in accordance with the type of the endoscope, a light sensing element provided for an endoscope-use camera and producing a light reception signal in accordance with a quantity of light received, a means for producing a correction signal from the information holding means when the endoscope is attached to the camera, and a means for controlling an exposure value on the basis of the light reception signal and correction signal delivered from a photographing unit.

DETAILED DESCRIPTION OF THE PREFERRED EMBODIMENT

Figure 1:
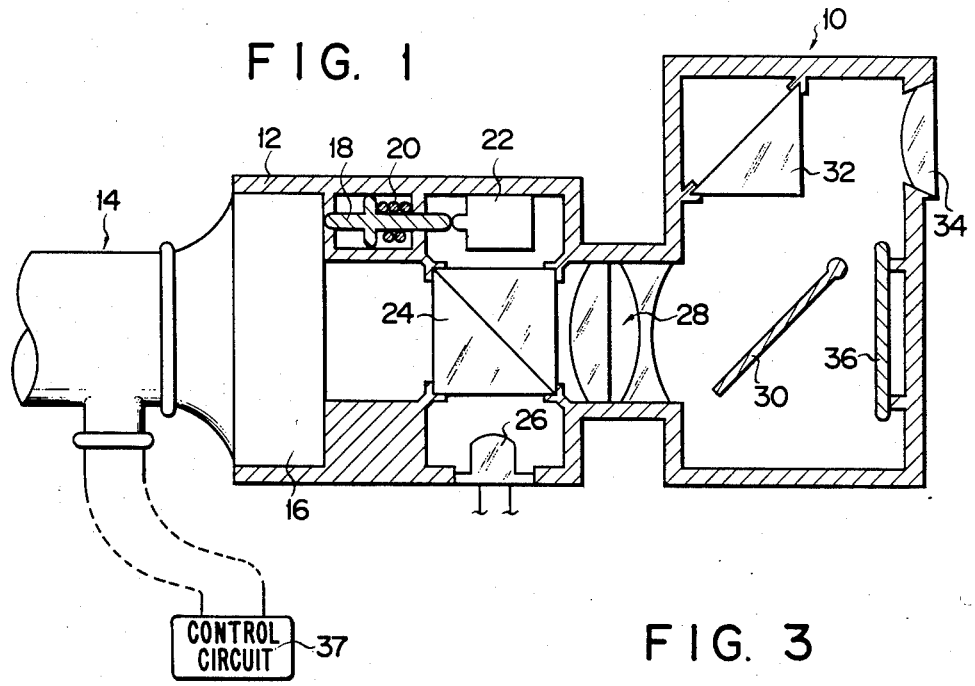
FIGS. 1 and 2 are partial sectional views showing a practical arrangement of a light reception signal and correction signal generating means according to an embodiment of this invention.

Now there will be described an embodiment of the automatic exposure control device for endoscope according to this invention with reference to the accompanying drawings. FIG. 1 shows a partial sectional view of a camera fitted with an endoscope. At one end of a camera body 10 is an endoscope mount 12 in and to which an eyepiece 16 of the endoscope 14 is inserted and fixed. The forward end of an actuator 18 protrudes against the fitting surface of the mount 12 in touch with the end face of the eyepiece section 16. The actuator 18, which is normally biased by a compression spring 20, is moved by the eyepiece section 16 against the biasing force of the spring 20 to change the switching state of a switching circuit 22 by means of the rear end of the actuator 18 (when the endoscope is set in place.) A correction signal produced by the switching circuit 22 will be described later. On the optical path of the camera body 10 is a beam splitter 24 which is composed of two prisms combined suitably. The beam splitter 24 transmits most of light from the endoscope 14, and also provides a spectral component of the light in a right-angled direction at a fixed rate. The branched light falls on a light sensing element 26 such as a photo diode attached to the side wall of the camera body 10. The light transmitted through the beam splitter 24 reaches a mirror 30 through a camera optics 28. The light reflected on the mirror 30 is transmitted to a camera eyepiece 34 through a prism 32. When a release button is depressed, the mirror 30 is lifted and a front curtain is driven, whereby the light from the endoscope 14 reaches a film 36.

Figure 2:
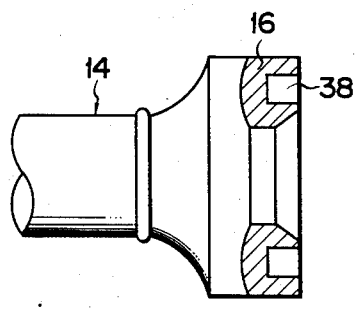

The other end of the endoscope 14 extends to an objective section (not shown).through a coupling section including an optical system for image transmission. Light from an external light source 37 is transmitted to the objective section through a light guide in the coupling section, and applied to the subject. The eyepiece section 16 of the endoscope 14 may or may not be provided with a notch 38 (FIG. 2) in a position corresponding to the actuator 18 depending on the type of endoscope (specifically, the thickness of the image transmitting optical system and the magnification of the eyepiece). In this embodiment, the notch 38 is provided in cases where the subject image is relatively large.

Figure 3:
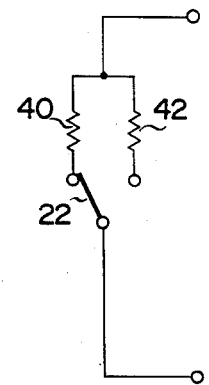
FIG. 3 is an electric circuit diagram of the means of FIG. 1.

Referring now to the drawing of FIG. 3, there is shown the electrical arrangement of the exposure control circuit. The switching element 22 has its first and second movable contact sides led respectively through resistors 40 and 42 to the control circuit 37 of a conventional light source unit (appearing in U.S. Pat. No. 4,153,356) for regular light control for a fixed input voltage.

The switching element 22, which is normally set to the first movable contact side, is switched to the second movable contact side by the rear end of the actuator 18 when the actuator 18 is pushed in. Here the resistance value of the resistor 42 is set below that of the resistor 40.

Now there will be described the operation of thus constructed automatic exposure control device for endoscope. Hereupon, let it be supposed that the endoscope employs narrow image transmitting optical system. That is, the eyepiece section 16 of the endoscope 14, as shown in FIG. 1, is not provided with the notch, so that, when the endoscope is attached to the mount 12 of the camera body 10, the actuator 18 is pushed in to turn the switching element 22 to the second movable contact side, and the resistor 42 with the smaller resistance value is connected with an input terminal to the control circuit of the light source unit. Thereafter, when the release button is depressed to drive the front curtain, the switch 22 as shown in FIG. 3 is closed, and the control circuit of the light source unit starts to operate If a thick image transmitting optical system is used with the endoscope, on the other hand, the eyepiece section 16 of the endoscope is to be provided with the notch 38 (see FIG. 2), so that the actuator 18 will not be pushed in although the endoscope is attached to the mount 12 of the camera body 10. As a result, with the switching element maintained on the first movable contact side, the input terminal to the control circuit of the light source unit is connected with the resistor 40 with the larger resistance value. Accordingly, the CR time constant is increased as compared with the case where the endoscope uses the narrow image transmitting optical system, so that the shutter speed will be lowered. Since the camera lens opening is supposed to be constant here, the deviation in the mean photometric quantity detected by the light sensing element depending on the size of the subject image may be corrected by controlling the shutter speed in accordance with the subject image size.

Figure 4:
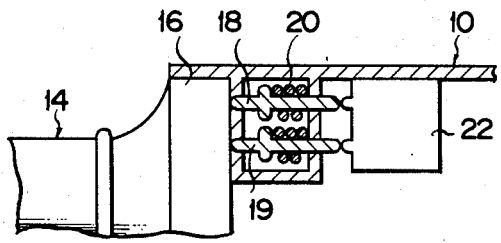
FIG. 4 is a partial sectional view of the principal part of the another practical example.
Figure 5:
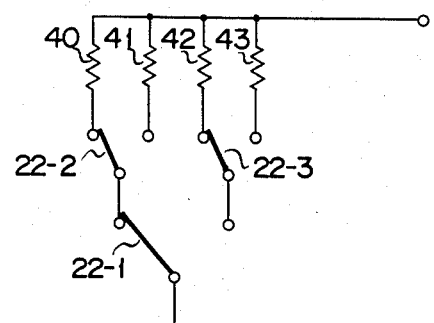
FIG. 5 is an electric circuit diagram of FIG. 4.

Although in this embodiment the switching circuit 22 can be set to only two switching states because the actuator 18 used is only one in number, further accurate exposure correction in compliance with the thickness of the image transmitting optical system of the endoscope may be achieved by two actuators 18 and 19 for four switching states, as shown in FIG. 4. FIG. 5 shows the principal part of the exposure control circuit for this case. In the switching circuit 22, which includes three switches 22-1, 22-2 and 22-3, the respective fixed contacts of the switches 22-2 and 22-3 are severally connected to two movable contacts of the switch 22-1, while the respective movable contacts of the switches 22-2 and 22-3 are led to the control circuit of the light source unit 37 through resistors 40, 41, 42 and 43. Thus, four resistance values are switched according to the states of the actuators 18 and 19, so that the exposure correction may be performed in four different manners in accordance with the thickness of the image transmitting optical system.

Figure 6:
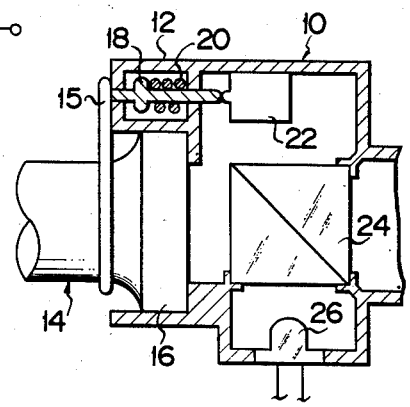
FIGS. 6 and 7 are partial sectional view of the principal parts of further practical examples.
Figure 7:
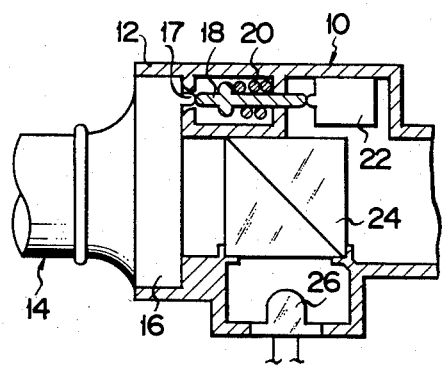

Referring now to FIGS. 6 and 7, there are shown practical examples according to this embodiment of this invention. Like reference numerals refer to the same parts throughout several views mentioned below, and the description of such same parts will be omitted. In the example of FIG. 6, the actuator 18, disposed at the outer periphery of the end face of the camera body 10, is so designed as to be pushed in by a jaw member 15 protruding from the outer periphery of the endoscope 14, thereby changing the switching state of the switch 22. Further, in the example of FIG. 7, the actuator 18 is pushed in by means of a projection 17 formed on the eyepiece section of the endoscope without projecting the actuator 18 against the mount 12.

Figure 8:
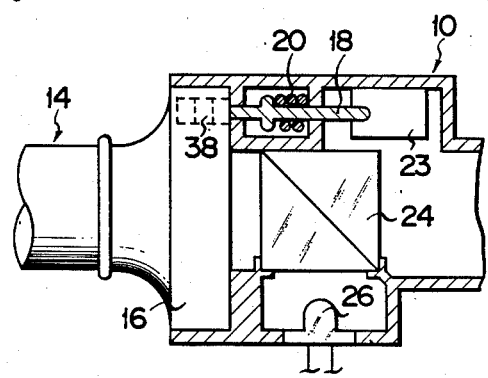
FIGS. 8 and 9 illustrate another embodiment of the invention.
Figure 9:
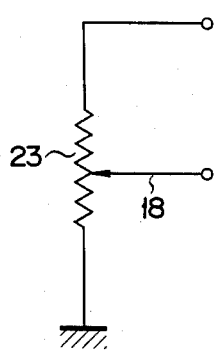

This invention is not limited to the above-mentioned embodiment. Referring now to FIGS. 8 and 9, there will be described a second embodiment. Here the actuator 18 used is only one in number like the case of the first embodiment, though a sliding resistor 23 is used in place of the switch 22, the rear end of the actuator 18 being joined together with the slider of the resistor 23. By varying the depth of the notch 38 in the eyepiece section 16 of the endoscope according to the thickness of the image transmitting optical system, as indicated by broken lines in FIG. 8, the resistance value of the sliding resistor may be determined according to the size of an image picture at the setting of the endoscope, and exposure correction values can be obtained successively.

Figure 10:
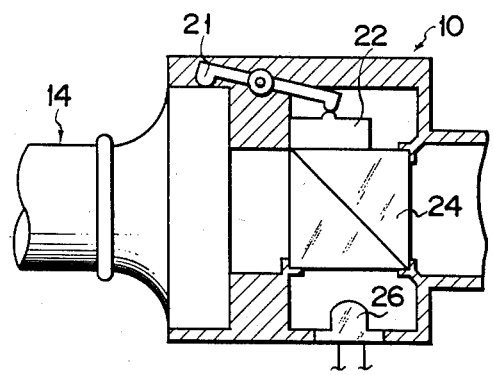
FIGS. 10 to 13 illustrate still another embodiment of the invention.
Figure 11:
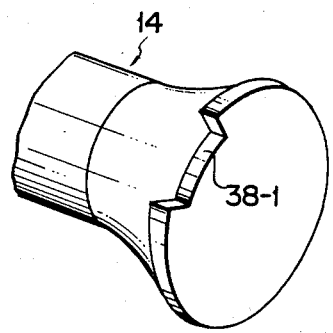
Figure 12:
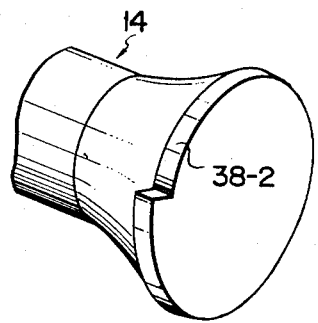

Referring further to FIGS. 10 to 12, there is shown a third embodiment, in which the endoscope is attached to the camera by bayonet coupling maintaining the predetermined relative position.

An actuator 21, which is pivotally mounted on the side of the mount, is so biased as to have its forward end projected against the inner side of the mount, the rear end thereof extending to the switch 22 inside the camera body. When using the endoscope 14 as shown in FIG. 11, the actuator 21, located inside a notch 38-1, will not turn the switch 22 on. When using the endoscope 14 as shown in FIG. 12, on the other hand, the actuator 21 has its forward end engaged with a notch 38-2, so that it will turn the switch 22 on. Thus, automatic exposure control may be achieved in accordance with the type of the endoscope, with the camera body attached to the endoscope by bayonet coupling that enables easy and secure attaching and detaching.

Figure 13:
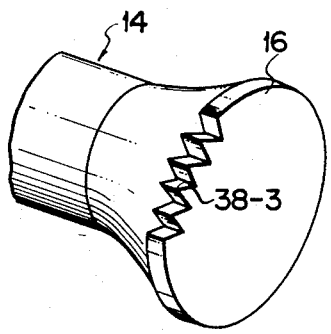

Further, as an alternative practical example, a sawtooth portion 38-3 may be formed on the eyepiece section 16 of the endoscope, as shown in FIG. 13, for the combined use with a gear at the mount portion of the camera. When the endoscope is bayonet-coupled, the saw-tooth portion 38-3 engages the gear. By rotating the gear, the slider of the sliding resistor is moved to change the resistance value. In this case, the number of teeth of the saw-tooth portion 38-3 varies with the thickness of the image transmitting optical system.

Although there have been described herein cases where the shutter speed alone is corrected with the camera lens opening kept constant, it is to be understood that the invention is not limited to those cases, and that exposure correction including the lens opening may also be performed. Moreover, capacitance values may be changed instead of changing the resistance values.

What is claimed is:

1. In combination, an endoscope having an image transmitting optical system and an eyepiece section at one end of the image transmitting optical system, a plurality of recesses located at the eyepiece section, the positions and numbers of said recesses representing in combination the size of a diameter of said image transmitting optical system which is indicative to said endoscope, and a camera for the endoscope, said camera having an attachment section for attachment to the eyepiece section of said endoscope for photographing an image whose size is determined by the diameter of said image transmitting optical system, signal generating means having a plurality of actuators provided at the attachment section of said camera and normally biased to extend toward the endoscope, said plurality of actuators each being independently reversed-biased if an end of the actuator does not coincide with a recess of the endoscope when the endoscope is attached to said camera to communicate the size of a field of view of said endoscope corresponding to the diameter of said image transmitting optical system to said camera and produce a correction signal corresponding to a combination of a bias state of said actuators, light receiving means provided within said camera for producing a light receiving signal corresponding to an amount of light reflected from a predetermined area of a film surface, and exposure means connected to said signal generating means and light receiving means for determining an exposure value in accordance with the light receiving signal and the correction signal.

2. The combination according to claim 1, in which said signal generating means includes a plurality of switches each actuated by a biasing force of said corresponding actuators and a voltage signal generator whose output voltage is determined by the switching state of the switches.

* * * * *

UNITED STATES PATENT AND TRADEMARK OFFICE
CERTIFICATE OF CORRECTION

PATENT NO. : 4,682,586
DATED : July 28, 1987
INVENTOR(S) : K. Matsuo

It is certified that error appears in the above-identified patent and that said Letters Patent are hereby corrected as shown below:

Title page:

[30] Foreign Application Priority Data
July 12, 1978 [JP] Japan.........53-84674

[63] Continuation of Ser. No. 5 4,881, July 5, 1979, abandoned.

Attorney, Agent or Firm - Balogh, Osann, Kramer, Dvorak, Genova & Traub

Signed and Sealed this

Ninth Day of February, 1988

*Attest:*

DONALD J. QUIGG

*Attesting Officer*      *Commissioner of Patents and Trademarks*